May 13, 1958 O. R. BRISTOW Plant Pat. 1,704
AZALEA PLANT
Filed May 6, 1957
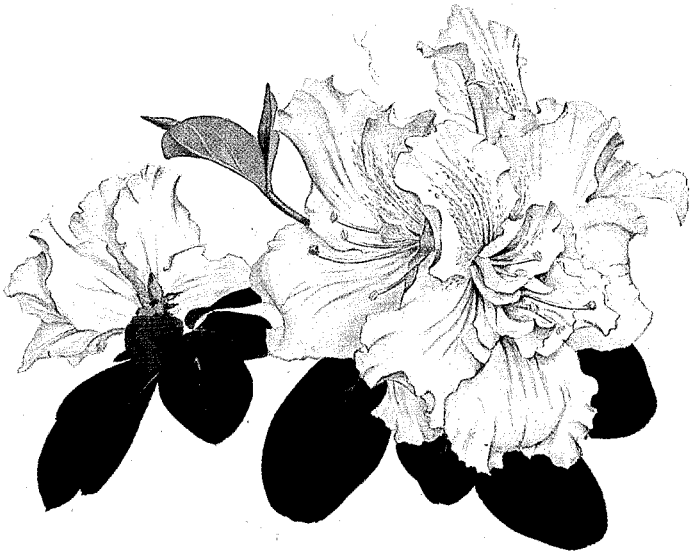
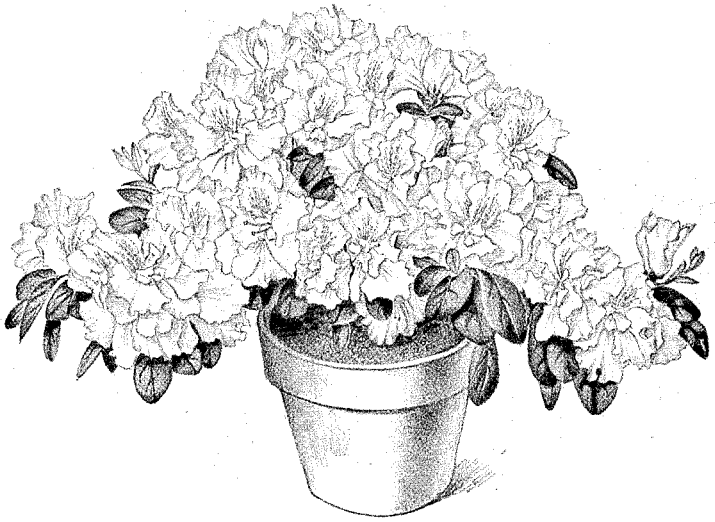
OWEN R. BRISTOW
INVENTOR.
BY Orville R. Seidner
AGENT United States Patent Office Plant Pat. 1,704
Patented May 13, 1958

1,704

AZALEA PLANT

Owen R. Bristow, San Bernardino, Calif., assignor to Mossholder Nursery, Orange County, Calif.

Application May 6, 1957, Serial No. 657,467
1 Claim. (Cl. 47—60)

This invention relates to a distinct and new variety of azalea plant reproduced as a result of deliberate experiments in hybridization carried out at my nursery in San Bernardino, California, the plant being derived from a cross-breeding of unpatented plants numbered 109B and 42 in my breeding records. This particular plant has been given the number 7A for identification purposes.

The orchid-like appearance of the flower, as will be noted in the accompanying illustration, together with the massive blooming of the plant due to its heavy bud setting quality, comprise the exceptional distinguishing characteristics of this azalea plant.

Of particular note with respect to the flower per se is the unusual red speckling in the throat of a pure white flower, as more particularly specified and described hereinbelow.

The plant itself grows easily and quickly, both indoors under glass and outdoors, and is quite readily forced in the greenhouse for any desired time from just prior to Christmas up to its normal blooming season in mid spring. The fast, many-branched growing quality of the plant is a further distinguishing characteristic with the dark green foliage on a compact bushy plant being quite attractive during the non-blooming season. By reason of the desirable forcing characteristic, together with striking appearance of the flowers, this plant is an exceptionally valuable addition to the growers' and nurserymen's lines, as well as those of the florists.

Asexual reproduction of this distinct and new azalea plant was accomplished by me at my nursery in San Bernardino, California, by the known method of removing cuttings from the original hybrid plant which matured from a seedling, and potting the cuttings separately from the donor plant. Subsequent reproductions of the plant in the same manner indicate that the foregoing characteristics, as well as further distinguishing characteristics set out below, are permanently fixed, and the accompanying illustration of a forced cutting grown plant shows the massive blooming of the unusual orchid-like flowers as well as their striking color characteristic.

The following is a detailed specification of the plant and flower, reference being had to the British Horticultural Chart of the British Colour Council for color identification of the flower and stigma, and to the Plochere Color System for color identification of the foliage:

*Plant*

Form of plant: Very bushy grower; symmetrical in form.
Growth habit: Rate of growth faster than Belgian Indica varieties; plants branch often, making bushy plants.
Rooting: Roots easily; very vigorous roots; grows well on own roots.
Blooming habit: Blooms prolifically when forced as well as outside plants in California; exceptionally heavy bud set; normally 3 flowers to a branch; when properly grown and forced into bloom, the flowers completely hide the foliage; blooms single flowers as well as single flowers with petaloids making some of the flowers semi-double.
Blooming season: March through April according to the weather; can be forced from mid-December through the blooming season.

Suitability for forcing: Holds flowers average well when forced; flowers bloom evenly when forced.

*Foliage*

Size: Average 1" wide, 2" long.
Quantity: Abundant.
Color: New foliage—Plate #1122 on upperside and Plate #1123 on underside; old foliage—exceptionally dark green, Plate #1129 on upperside and Plate #1130 on underside.
Shape: Oval (rounded on end).
Texture: Lighter than normal.
Edge or margin: Smooth.
Ribs and veins: Normal.
Aspect: Attractive, glossy, dark green foliage, slightly larger than average.

*Flower*

Size: Average 3" across flower; 3½" from top to bottom edge.
Flowers borne: Normally 3 on each stem.
Quantity of bloom: Exceptionally abundant.
Continuity: Individual flowers last the same length of time as most Belgian Indicas, but the fact that it sets such a heavy crop of buds keeps the plant blooming for longer periods of time than most Belgian Indicas.
Petalage:
*Size.*—Average 1¼" wide, 2" long.
*Number of petals under normal conditions.*—5.
*Color of bud.*—White with light greenish cast at base of bud.
*Color of open flower.*—The 2 bottom petals are pure white; the 3 top petals are also pure white and speckled with red from the throat to within ¼" of the top of the petals. When petaloids show in throat of flower, they are also speckled with red. Plate #025/1 and #025/2.
*Texture.*—Light.
*Appearance.*—The upper three petals are heavily ribbed on the back which holds them erect. The two bottom petals are not heavily ribbed with the result they hang loosely giving the flower an orchid-like appearance.
Shape: Ruffled or frilled edge. The flower's height is greater than the width. Single to semi-double flowers.
Arrangement: Solid mass of flowers.
Persistence: Sets a heavy set of buds and all new growth sets buds.

*Reproductive organs*

Stamens: From 8 to 12; some flowers have partial petaloidy of stamens.
Anther: Creamy colored—normal.
Filament: White—normal.
Styles: White.
Stigma: Pale greenish-yellow, Plate #861/3.
Ovary: Normal.

Having illustrated and described the invention or discovery, what is claimed as new and patentable is:

A distinct and new variety of azalea plant, substantially as illustrated and described hereinabove, and characterized generally by the ease and rapidity with which the plant may be grown outdoors or as forced under glass, the plant being distinguished by its bushy and many-branched feature with attractive dark green glossy foliage, and particularly characterized by the heavy and prolonged bud setting quality resulting in continuing massive blooming of orchid-like pure white flowers having distinctive red speckling in their throats.

No references cited.